United States Patent [19]

Buysch et al.

[11] Patent Number: 5,502,232
[45] Date of Patent: Mar. 26, 1996

[54] PROCESS FOR PREPARING DIARYL CARBONATES

[75] Inventors: Hans-Josef Buysch, Krefeld; Joachim Dohm, Köln; Carsten Hesse, Krefeld; Johann Rechner, Krefeld; Dieter Kaufmann, Goslar, all of Germany

[73] Assignee: Bayer Aktiengesellschaft, Leverkusen, Germany

[21] Appl. No.: 339,613

[22] Filed: Nov. 15, 1994

[30] Foreign Application Priority Data

Nov. 22, 1993 [DE] Germany ............... 43 39 697.6
Dec. 9, 1993 [DE] Germany ............... 43 41 990.9

[51] Int. Cl.$^6$ .................................. C07C 69/96
[52] U.S. Cl. ............... 558/270; 558/271; 558/274; 558/275
[58] Field of Search ............... 558/270, 271, 558/274, 275

[56] References Cited

U.S. PATENT DOCUMENTS

| 4,201,721 | 5/1980 | Hallgren | 558/260 |
| 5,336,803 | 8/1994 | Kezuka et al. | 558/277 |

FOREIGN PATENT DOCUMENTS

| 0350700 | 1/1990 | European Pat. Off. . |
| 0503581 | 9/1992 | European Pat. Off. . |
| 2738437 | 4/1978 | Germany . |
| 2815512 | 10/1979 | Germany . |
| 1578713 | 11/1980 | United Kingdom . |
| WO93/03000 | 2/1993 | WIPO . |

OTHER PUBLICATIONS

Chemical Abstracts–10th Coll, 1 page; DE 2,815,512; GB 1,578,713; CA#92:163723b, 1979.

Journal of Organometallic Chemistry, vol. 212, 1981, pp. 135–139; "The palladium-catalyzed synthesis of diphenyl . . . ", J. E. Hallgren et al.

*Primary Examiner*—Jose G. Dees
*Assistant Examiner*—Dwayne C. Jones
*Attorney, Agent, or Firm*—William C. Gerstenzang; Sprung Horn Kramer & Woods

[57] ABSTRACT

Diaryl carbonates can be prepared by reacting aromatic hydroxy compounds with CO and $O_2$ at elevated temperature over a noble metal catalyst in the presence of a base, a quaternary salt, a cocatalyst and a dessicant. According to the invention, the noble metal catalyst is activated with CO in the presence of the quaternary salt and optionally in the presence of the cocatalyst. In a particular process variant, the base used is a preformed alkali metal phenoxide.

20 Claims, No Drawings

PROCESS FOR PREPARING DIARYL CARBONATES

BACKGROUND OF THE INVENTION

1. Field of the Invention

The present invention relates to a process for preparing diaryl carbonates by reaction of an aromatic hydroxy compound (e.g. phenol) with carbon monoxide and oxygen at elevated temperature in the presence of a base, a quaternary salt, a dessicant, a catalyst and a cocatalyst, which is characterized in that the catalyst is activated prior to the reaction. In a particular process variant, the base used is a preformed alkali metal phenoxide.

2. Description of the Related Art

It is known that aromatic carbonates can be prepared by oxidative reaction of an aromatic hydroxy compound with carbon monoxide in the presence of a homogeneous noble metal catalyst (German Offenlegungsschrift 28 15 512). The noble metals proposed are the elements of group VIIIb, with a preference being given to using palladium. During the reaction, this palladium(II) species is reduced to palladium(0) and reoxidized by oxygen with the aid of a cocatalyst to give palladium(II) again. Cocatalysts which can be used are, for example, various manganese or cobalt salts in different oxidation states. Besides these cocatalysts, use is made of a base, a phase-transfer catalyst and a dessicant. Methylene chloride is preferably used as solvent. According to German Offenlegungsschrift 27 38 437, sterically hindered tertiary amines are used as base and a molecular sieve is used as dessicant.

Disadvantages of these processes are, besides the use as solvent of the toxic, volatile methylene chloride which requires a high level of safety precautions and has to be recovered at considerable cost, long reaction times and the poor space-time yields associated therewith. However, for an industrial reaction, the insufficient reproducibility proves to be the actually decisive disadvantage, since the same procedure can give, from batch to batch, completely different results, even complete failure of the catalysis.

The high price and the oxidative instability of the sterically hindered tertiary amine bases proposed in German Offenlegungsschrift 27 38 437 is a further disadvantage of this process. Recovery of the base is technically complicated. In addition, a considerable part of the base is decomposed during the long reaction times, so that large amounts of the expensive base continually have to be replaced, which makes an economical utilization of the process difficult.

J. E. Hallgren and G. M. Lucas in Journal of Organometallic Chemistry 212 (1981) 135–139 report the use of aqueous sodium hydroxide solution as base. In the presence of small amounts of 50% strength aqueous sodium hydroxide solution and a phase-transfer catalyst, Hallgren and Lucas observe an increase in the reaction rate, compared with the use of tertiary amines. A considerable disadvantage of this procedure is the fact that aromatic carbonates, which are to be prepared by this process, are rapidly decomposed by aqueous sodium hydroxide solution (Ullmanns Encyclopädie, 5th edition, vol. A5, pp. 197–202). The cleavage reaction of aromatic carbonates proceeds so quickly in the presence of even catalytic amounts of aqueous sodium hydroxide solution that only low carbonate concentrations can be achieved in the reaction system. In addition, in this case too, the toxic, volatile methylene chloride is used as solvent, which brings with it the above described problems. Furthermore, the simultaneous presence of methylene chloride and sodium hydroxide results in a particular danger, since these, as is known to those skilled in the art, react to give highly reactive dichlorocarbene which leads to secondary reactions, and may even react spontaneously and explosively. Owing to this uncontrollable reaction, industrial use of this process is not possible either. In addition, these measures do not improve the reproducibility.

European Patent Specification 503 581 proposes the use of various copper salts as cocatalyst. Besides this cocatalyst, the use of considerable amounts of various quinones/hydroquinones as electron-transfer catalyst is also proposed. These measures do not improve the reproducibility. The industrial use of this process is therefore not possible either. In addition, this process likewise uses methylene chloride as solvent. The separation of the electron-transfer catalyst from the reaction mixture requires considerable additional expense in this process. Furthermore, hydroquinones are aromatic bifunctional hydroxy compounds which can be converted into carbonates in the same manner as phenol. The separation of the byproducts formed in this way can only be achieved at great expense. Recovery of the electron-transfer catalyst used is thus not possible. The formation of the byproducts would, at a given reproducibility, considerably lower the selectivity and thus the economics of this process.

The application WO 93/03000 describes a process for preparing aromatic carbonates which does omit the use of a solvent, but still requires considerable amounts of cocatalyst and electron-transfer catalyst. This too does not solve the problem of the insufficient reproducibility, so that all in all an industrially useable process has not hitherto been available.

It is therefore an object of the invention to find a process which allows the synthesis of aromatic carbonates to be carried out reproducibly under industrially achieveable conditions.

SUMMARY OF THE INVENTION

It has now surprisingly been found that the preparation of diaryl carbonates can be reproducibly carried out by oxidative carbonylation of an aromatic hydroxy compound in the presence of a noble metal catalyst, a cocatalyst, a dessicant, a quaternary salt and a base without addition of an electron-transfer catalyst if the noble metal catalyst is, prior to the reaction, activated with carbon monoxide in the presence of the quaternary salt in a liquid phase, i.e. a solvent or the aromatic hydroxy compound alone or in a mixture of solvent and aromatic hydroxy compound. This activation of the noble metal catalyst leads not only to good reproducibility of the reactions, but also surprisingly to an increase in the space-time yields.

It has further been found that the above described activation is also successful without limitation in the presence of the cocatalyst which was hitherto not required.

If the noble metal catalyst is activated additionally in the presence of the cocatalyst which was hitherto not required, this has the advantage that after the work up is complete, the noble metal and cocatalyst can be recycled together and complicated separation operations can be omitted.

The invention accordingly provides a process for preparing an organic carbonate of the formula (I)

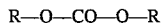

in which

R is an optionally substituted $C_6$–$C_{12}$-aryl, preferably an optionally substituted $C_6$-aryl, particularly preferably phenyl, by reaction of an aromatic hydroxy compound of the formula (II),

   (II), where

R is as defined above,
with carbon monoxide and oxygen at 30°–200° C., preferably 30°–150° C., particularly preferably 40°–120° C., and at a pressure of 1–80 bar, preferably 2–50 bar, particularly preferably 5–25 bar, in the presence of a compound of a noble metal of the group VIIIB as catalyst, a cocatalyst selected from the group consisting of the metal compounds of the groups IIIA, IVA, VA, IB, IIB, VIB and VIIB of the Periodic Table of the Elements (Mendeleev), a quaternary salt, a dessicant and a base, which is characterized in that the noble metal catalyst is, prior to the reaction, activated by treatment with carbon monoxide in a liquid phase at a temperature of 15°–200° C., preferably 20°–150° C., particularly preferably 40°–100° C. and a pressure of 1–300 bar, preferably 1–200 bar, particularly preferably 1–150 bar, in the presence of the quaternary salt and in the presence or in the absence of the cocatalyst, with the noble metal catalyst being present in the activation mixture in an amount of 0.0001–30% by weight, based on the total reaction mixture.

DETAILED DESCRIPTION OF THE INVENTION

For the example of the formation of diphenyl carbonate (DPC), the process of the invention can be represented as follows by means of formulae:

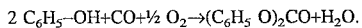

For the activation, the noble metal catalyst whose amount in the process of the invention is not limited, but is preferably present in such an amount that the concentration of the metal in the activation mixture is from 0.0001 to 30% by weight, particularly preferably 0.001 to 10% by weight, is dissolved in an inert solvent or directly in the melt of the aromatic hydroxy compound or in mixtures of both.

The cocatalyst whose amount is not limited in the activation of the invention, but is preferably present in the activation mixture in the range from 0 to 40% by weight; preference is given to an amount of from 0.005 to 10% by weight, particularly preferably 0.01 to 4% by weight, based on the activation mixture.

The cocatalyst is not necessary for the activation of the noble metal catalyst, but also does not interfere with it. The addition of the cocatalyst at this point, however, facilitates a continuous mode of reaction, since (i) a separate metering of the cocatalyst can be omitted, and (ii), for the working-up of the reaction solutions, noble metal and cocatalyst need not to be separated.

Suitable solvents for the activation of the invention which may be mentioned are aliphatic hydrocarbons, cycloaliphatic hydrocarbons, aromatic hydrocarbons, halogenated hydrocarbons, such as, for example, methylene chloride, ethers and esters.

To this solution there is added a quaternary salt which is, for example, an ammonium or phosphonium salt substituted by organic radicals. Suitable salts for use in the process of the invention are ammonium and phosphonium salts which bear, as organic radicals, $C_6$- to $C_{10}$-aryl, $C_7$- to $C_{12}$-aralkyl and/or $C_1$- to $C_{20}$-alkyl radicals and whose anion is a halide, tetrafluoroborate or hexafluorophosphate. In the process of the invention, preference is given to using ammonium salts which bear, as organic radicals, $C_6$- to $C_{10}$-aryl, $C_7$- to $C_{12}$-aralkyl and/or $C_1$- to $C_{20}$-alkyl radicals and whose anion is a halide, particular preference is given to tetrabutylammonium bromide.

This solution is subsequently treated, at from 15° to 200° C., preferably at from 20° to 150° C., particularly preferably at from 40° to 100° C., with carbon monoxide. This can be achieved either by passing in carbon monoxide at atmospheric pressure in an amount of from 0.1 to 250 l/h, preferably from 0.5 to 200 l/h, particularly preferably from 1 to 100 l/h, per gram of the noble metal used, or by treating the solution with carbon monoxide in an autoclave under a pressure of from 1 to 300 bar, preferably from 1 to 200 bar, particularly preferably from 1 to 150 bar. The activation time depends slightly on the noble metal catalyst used and on any inert solvent which is optionally used. It is generally from a few minutes to a number of hours, for example 0.05–5 h, preferably 0.1–3 h, particularly preferably 0.25–2 h. In the process of the invention, the noble metal catalyst can be activated directly prior to the reaction, but it can also be isolated and stored after removal of the solvent or of the aromatic hydroxy compound, for example, by distillation. This noble metal catalyst which has been activated once remains stable in air even after months and can be used without loss in activity. Storage in dissolved form is also possible. A further embodiment of the process of the invention can comprise activating the noble metal catalyst in the manner described above and then adding this solution all at once or in a plurality of portions to the reaction system.

The aromatic hydroxy compounds to be used in the process of the invention are aromatic hydroxy compounds which are derived from $C_6$–$C_{12}$-aromatics, such as benzene, naphthalene or biphenyl, and can be monosubstituted or disubstituted by $C_1$–$C_4$-alkyl, $C_1$–$C_4$-alkoxy, fluorine, chlorine or bromine, preferably phenol, o-, m- or p-cresol, o-, m- or p-chlorophenol, o-, m- or p-ethylphenol, o-, m- or p-propylphenol, o-, m- or p-methoxyphenol, 2,6-dimethylphenol, 2,4-dimethylphenol, 3,4-dimethylphenol, 1-naphthol and 2-naphthol, particularly preferably phenol.

The process of the invention is preferably carried out without solvent. Of course inert solvents may also be used. Examples of these which may be mentioned are the same as those mentioned above for the activation.

The noble metal catalysts suitable for the process of the invention comprise at least one metal of the group VIII, preferably palladium. In the process of the invention, it can be added in various forms. Palladium can be used in metallic form or preferably in the form of palladium compounds of the oxidation states 0 and +2, such as, for example, palladium(II) acetylacetonate, halides, carboxylates of $C_2$–$C_6$-carboxylic acids, nitrate, oxides or palladium complexes which can contain, for example, olefins, amines, phosphines and halides. Particular preference is given to palladium bromide, palladium(II) acetylacetonate and palladium acetate.

The amount of noble metal catalyst is not limited in the process of the invention. Preferably, sufficient catalyst is added for its concentration, calculated as metal, in the reaction mixture to be from 10 to 3000 ppm, particular preference is given to concentrations of from 50 to 1000 ppm.

The cocatalyst used for the process of the invention is a metal compound of the groups IIIA, IVA, VA, IB, IIB, VIB or VIIB of the Periodic Table of the Elements (Mendeleev), with the metal being able to be used in various oxidation states. Without limiting the process of the invention, mention may be made of manganese (II), manganese (III), copper (I), copper (II), cobalt (II), cobalt(III), vanadium(III) and vanadium(IV). The metals can be used, for example, as halides, oxides, carboxylates of $C_2$–$C_6$-carboxylic acids, diketonates or nitrates and also as complex compounds which can contain, for example, carbon monoxide, olefins, amines, phosphines and halides. In the process of the invention, preference is given to using manganese(II) compounds, particularly preferably manganese(II) complexes, very particularly preferably manganese(II) acetylacetonate.

The cocatalyst is used in such an amount that its concentration is in the range from 0.001 to 20% by weight of the reaction mixture, the concentration range is preferably from 0.005 to 5% by weight, particularly preferably 0.01 to 2% by weight. The cocatalyst may be added commonly with the activated noble metal catalyst or, less preferred, separately.

Dessicants for the process of the invention are preferably inert and of the type known to those skilled in the art for binding water. They can be classified into regenerative and non-regenerative, liquid or solid, chemically reactive, i.e. those which form a new compound or a hydrate, physically absorptive having a constant or variable relative moisture content in the adsorbent, etc. Preferably, the dessicant(s) used in the process of the invention has/have a high capacity and/or effectiveness, preferably both, in the removal of moisture from the reaction medium. The term "capacity" used in the present application relates to the amount of water which can be taken up by a given weight of the dessicant, and the term "effectiveness" relates to the degree of drying which can be achieved by such a dessicant. Examples of such dessicants are, without limiting the process of the invention to these examples, activated aluminium oxide, barium oxide, calcium oxide, calciumchloride, calciumsulphate, lithium chloride, sodium sulphate, magnesium sulphate and natural or synthetic hydrophilic aluminosilicates of the zeolite type (molecular sieves). Preferred dessicants for use in the process of the invention are natural or synthetic hydrophilic aluminosilicates of the zeolite type (molecular sieves). Particular preference is given to using zeolites of type A or faujasite.

In the process of the invention, that amount of dessicant is used which is sufficient to take up the water of reaction formed and the moisture of the starting materials. This amount depends on capacity and effectiveness of the dessicant used in each case and can be calculated in each case by those skilled in the art. Thus, it is known, for example, that zeolite A can be expected to have a water uptake of 20–30% of its dry weight. According to the invention, use is made of an amount of dessicant which corresponds to 100–800%, preferably 200–600% of the expected amount of water to be taken up. If less than this amount of dessicant is used, poorer results are obtained; if more dessicant is used than is indicated by the upper limit, the economics of the process become questionable, since a large amount of dessicant is circulated without being utilized. The upper limit, the absolute amount of dessicant and thus also the conversion to carbonates (I) to be expected are also limited by the need for the reaction mixture to remain stirrable or otherwise mixable. In general, an amount of from 1 to 30% by weight, based on the reaction mixture, is used.

The quaternary salt in the process of the invention is as defined above for the catalyst activation. The salts used for activation and carrying out the process can be identical or different, but are preferably identical for the purposes of simplifying the work up.

The amount of such a quaternary salt is from 0.1 to 50% by weight, based on the weight of the reaction mixture. This amount is preferably from 0.5 to 15% by weight, particularly preferably from 1 to 5% by weight.

The bases used in the process of the invention can be tertiary amines or alkali metal hydroxides or carbonates. Suitable tertiary amines are those which bear, as organic radicals, $C_6$- to $C_{10}$-aryl, $C_7$- to $C_{12}$-aralkyl and/or $C_1$- to $C_{20}$-alkyl radicals, for example triethylamine, tripropylamine, tributylamine, trioctylamine, benzyldimethylamine, dioctylbenzylamine, dimethylphenethylamine, 1-dimethylamino-2-phenylpropane; tertiary a mines for the process of the invention are furthermore cyclic aromatic or non-aromatic amines such as pyridine, N-methylpiperidine, 1,2,2,6,6-pentamethylpiperidine. Particular preference is given to sterically hindered tertiary amines, e.g. diisopropylethylamine or 1,2,2,6,6-pentamethylpiperidine.

The base is added in an amount which is independent of the stoichiometry. The ratio of palladium to base is preferably selected so that from 0.1 to 5, preferably from 0.5 to 2, particularly preferably from 0.9 to 1.3 equivalents of base are used per mole of palladium.

In a particular process variant, the base used is advantageously a preformed alkali metal phenoxide or a solution of a preformed alkali metal phenoxide. This is very surprising, since the use of alkali metal hydroxides or tertiary amines in the reaction mixture should lead to the formation of phenoxides. However, if preformed alkali metal phenoxides are used as base under otherwise identical conditions, significantly higher selectivities and space-time yields are achieved than when tertiary amines or alkali metal hydroxides are used. There is at present no explanation for this phenomenon. It is assumed that the precipitation of catalyst and cocatalyst occurring in the presence of basic compounds by means of phenoxide anions proceeds differently than by means of tertiary amines, alkali metal hydroxides or carbonates. The precipitation occurring by means of phenoxide anions obviously gives a higher activity. In those systems in which phenoxide anions can be formed from aromatic hydroxy compounds and tert-amines or alkali metal hydroxides or carbonates, the formation of a less active precipitation obviously proceeds so quickly that any phenoxide formed can no longer correct this fact. This discovery is very surprising.

Alkali metal phenoxides which can be used in the process of the invention are alkali metal salts of aromatic hydroxy compounds of the formula (II) in which R is as defined above. Very particular preference is given to using an alkali metal salt of that aromatic hydroxy compound which is also to be converted into organic carbonate.

Suitable cations for the alkali metal phenoxides of the invention are the alkali metals lithium, sodium, potassium, rubidium or caesium. Preference is Given to using lithium, sodium and potassium phenoxides, particularly preferably sodium and potassium phenoxide.

The alkali metal phenoxide can be added to the reaction mixture as a pure compound in solid form or as a melt. The hydrates of the alkali metal phenoxides can of course also be used in the process of the invention. An example of such a hydrate which may be mentioned here, without limiting the process of the invention, is sodium phenoxide trihydrate. The amount of added water is generally such that a maximum of 5 mol of water are used per mole of phenoxide. Higher water concentrations lead, inter alia, to poorer conversions and decomposition of carbonates formed, as in the case of the aqueous sodium hydroxide solution proposed by HallGren. Preference is given to using a maximum of 2 mol of water, in particular a maximum of 1 mol of water, per mole of phenoxide. Particular preference is Given to using essentially anhydrous phenoxides as are, for example, available in industry.

In a further embodiment of the invention, the alkali metal phenoxide is added to the reaction mixture as a solution containing from 0.1 to 80% by weight, preferably from 0.5 to 65% by weight, particularly preferably from 1 to 50% by weight, of the alkali metal phenoxide. Solvents which can be used here are $C_1$-$C_8$-alcohols or phenols (II), and also further solvents. Examples of further solvents which may be mentioned are dimethylacetamide, N-methylpyrrolidinone, tetramethylurea, ether alcohols such as diethylene glycol, halogenated hydrocarbons such as chlorobenzene or dichlorobenzene, and ethers such as dioxane. These solvents can be used alone or in any combination with one another. One embodiment of the process of the invention thus comprises, for example, dissolving the phenoxide in a phenol melt which has been diluted with an inert solvent. The alkali metal phenoxide is preferably dissolved in the melt of an aromatic hydroxy compound. Particularly preferably, the alkali metal phenoxide is dissolved in a melt of that aromatic hydroxy compound which is to be converted into the organic carbonate. Very particular preference is given to dissolving the alkali metal phenoxide in phenol.

Such solutions can be obtained, for example, by combining the alkali metal phenoxide directly with the solvent. It is naturally also possible to react alkali metals, alkali metal (hydro)oxides or alkoxides with phenol, optionally in the presence of an additional inert solvent, to give the alkali metal phenoxide, to remove the water or alcohol thus formed by, for example, distillation and in this way to obtain a solution of an alkali metal phenoxide which can be used in the process of the invention.

The amount of phenoxide is not critical. The ratio of noble metal to phenoxide is preferably selected such that from 0.1 to 500, preferably from 0.5 to 200, particularly preferably from 0.9 to 130, equivalents of phenoxide are used per mole of noble metal.

The process of the invention is carried out, preferably without solvent, at from 30° to 200° C., preferably at from 30° to 150° C., particularly preferably at from 40° to 120° C., at a pressure of from 1 to 80 bar, preferably from 2 to 50 bar, particularly preferably from 5 to 25 bar.

The composition of the reaction Gases carbon monoxide and oxygen can be varied within wide concentration limits, but a $CO:O_2$ molar ratio (standardized to CO) of 1:(0.001–1.0), preferably 1:(0.01–0.5) and particularly preferably 1:(0.02–0.3), is advantageously set. With these molar ratios, the oxygen partial pressure is sufficiently high for high space-time yields to be able to be achieved and at the same time for no explosive carbon monoxide/oxygen gas mixtures to be able to be formed. The reaction gases are subject to no particular purity requirements, so that synthesis gas serves as CO source and air serves as $O_2$ carrier; care only needs to be taken that no catalyst poisons such as, for example, sulphur or compounds thereof are introduced. In the preferred embodiment of the process of the invention, pure CO and pure oxygen are used.

The process of the invention can be performed in different variants. One possibility comprises carrying out the process batchwise in conventional stirred vessels or autoclaves. In this variant, CO and oxygen are introduced into the reaction mixture either via a gassing stirrer or other known gas distribution devices. After achieving the optimum conversion, the reaction mixture is worked up, for example by distillation, with the aromatic hydroxy compound being removed first and the aromatic carbonate being isolated in a further step. The catalyst components and the dessicant present in the residue can be recovered and recycled using conventional measures.

The following examples illustrate the process of the invention, without, however, limiting it to these.

Example 1

Catalyst activation

In a reactor, 0.133 g of palladium bromide and 3.2 g of tetrabutylammonium bromide were dissolved at 55° C. in 100 g of phenol containing 750 ppm of $H_2O$ ($\Delta$ 4 mmol of $H_2O$/100 g). Carbon monoxide (3 l/h) was passed in for one hour by means of a gassing stirrer, the reaction mixture becoming orange in colour.

Reaction procedure

To the solution of the activated catalyst were added 4 g of zeolite A (Baylith L 133 from Bayer AG), 0.153 g of manganese(II) acetylacetonate and 0.403 g of 1,2,2,6,6-pentamethylpiperidine. A gas mixture (12 l/h) comprising carbon monoxide and air (1:1) was then passed in for 6 hours and the reaction mixture was subsequently analysed by gas chromatography. The analysis indicated that 1.5% of diphenyl carbonate was present in the reaction mixture.

Assuming that the binding capacity of the zeolite A for $H_2O$ is 20% of its weight, 4 g of zeolite A can bind 0.8 g =44 mmol of $H_2O$. That gives, subtracting 4 mmol of $H_2O$ in the phenol used, a capacity of 40 mmol for water of reaction. 1.5% of diphenyl carbonate correspond to 1.62 g or 7.57 mmol. The 7.57 mmol of water of reaction loaded the zeolite A to about 19% of its capacity of 40 mmol of $H_2O$. The zeolite A was thus present in an amount of about 530% of the required amount.

This experiment was, as described, repeated. The analysis indicated that 1.55% of diphenyl carbonate was present in the reaction mixture. A further repetition again gave 1.5% of diphenyl carbonate in the reaction mixture.

Comparative Example 1

In a reactor, 0.133 g of palladium bromide, 3.2 g of tetrabutylammonium bromide, 4 g of zeolite A (Baylith L 133 from Bayer AG), 0.153 g of manganese(II) acetylacetonate and 0.403 g of 1,2,2,6,6-pentamethylpiperidine were dissolved at 55° C. in 100 g of phenol. As described in Example 1, a gas mixture comprising carbon monoxide and air was then passed in for 6 hours and the reaction mixture was subsequently analysed by gas chromatography. The analysis indicated that 0.25% of diphenyl carbonate was present in the reaction mixture.

This experiment was repeated in the same manner using fresh catalyst. The analysis indicated that no diphenyl carbonate was present in the reaction mixture.

This experiment was then again repeated as described and again using fresh catalyst. The analysis after a reaction time of 6 hours indicated that 0.8% of diphenyl carbonate was present in the reaction mixture.

These examples show that no reproducible results can be achieved.

Example 2

The catalyst activation was carried out as described in Example 1.

To the solution of the activated catalyst were added 4 g of zeolite A (Baylith L 133 from Bayer AG), 0.153 g of manganese(II) acetylacetonate and 0.4 ml of 50% strength aqueous sodium hydroxide solution. A gas mixture (12 l/h) comprising carbon monoxide and air (1:1) was then passed in for 6 hours and the reaction mixture was subsequently analysed by gas chromatography. The analysis indicated that 1.4% of diphenyl carbonate was present in the reaction mixture.

The $H_2O$ content of the sodium hydroxide solution corresponded to 11 mmol. The remaining $H_2O$ binding capacity of the zeolite A was thus 29 mmol. 1.4% of diphenyl carbonate correspond to 6.5 mmol. The $H_2O$ binding capacity was thus 22% utilized. The zeolite A was therefore present in an amount of 455% of the required amount.

This experiment was repeated as described. The analysis indicated that 1.36% of diphenyl carbonate was present in the reaction mixture.

Example 3

Catalyst activation

In a reactor, 0.133 g of palladium bromide, 0.153 g of manganese(II) acetylacetonate and 3.2 g of tetrabutylammonium bromide were dissolved at 55° C. in 100 g of phenol containing 750 ppm of $H_2O$ (Δ 4 mmol of $H_2O$/100 g). Carbon monoxide (3 l/h) was passed in for one hour by means of a gassing stirrer.

Reaction Procedure

To the solution of the activated catalyst were added 4 g of zeolite A (Baylith L 133 from Bayer AG) and 0.4 ml of 25% strength aqueous sodium hydroxide solution. A gas mixture (12 l/h) comprising carbon monoxide and air (1:1) was then passed in for 6 hours and the reaction mixture was subsequently analysed by gas chromatography. The analysis indicated that 1.4% of diphenyl carbonate was present in the reaction mixture.

This experiment was, as described, repeated. The analysis indicated that 1.5% of diphenyl carbonate was present in the reaction mixture.

Example 4

Catalyst activation

In a reactor, 0.152 g of palladium acetylacetonate, 0.153 g of manganese(II) acetylacetonate and 3.2 g of tetrabutylammonium bromide were dissolved at 55° C. in 100 g of phenol containing 750 ppm of $H_2O$ (≙ 4 mmol of $H_2O$/100 g). Carbon monoxide (3 l/h) was passed in for one hour by means of a gassing stirrer.

Reaction procedure

To the solution of the activated catalyst were added 4 g of zeolite A (Baylith L 133 from Bayer AG) and 0.4 ml of 25% strength aqueous sodium hydroxide solution. A gas mixture (12 l/h) comprising carbon monoxide and air (1:1) was then passed in for 6 hours and the reaction mixture was subsequently analysed by gas chromatography. The analysis indicated that 1.55% of diphenyl carbonate was present in the reaction mixture.

This experiment was repeated as described. The analysis indicated that 1.45% of diphenyl carbonate was present in the reaction mixture.

Example 5

Catalyst activation

In a reactor, 0.112 g of palladium acetate, 0.153 g of manganese (II) acetylacetonate and 3.2 g of tetrabutylammonium bromide were dissolved at 55° C. in 100 g of phenol containing 750 ppm of $H_2O$ (≙ 4 mmol of $H_2O$/100 g). Carbon monoxide (3 l/h) was passed in for one hour by means of a gassing stirrer.

Reaction procedure

To the solution of the activated catalyst were added 4 g of zeolite A (Baylith L 133 from Bayer AG) and 0.4 ml of 25% strength aqueous sodium hydroxide solution. A gas mixture (12 l/h) comprising carbon monoxide and air (1:1) was then passed in for 6 hours and the reaction mixture was subsequently analysed by gas chromatography. The analysis indicated that 1.2% of diphenyl carbonate was present in the reaction mixture.

This experiment was, as described, repeated. The analysis indicated that 1.25% of diphenyl carbonate was present in the reaction mixture.

Example 6

Catalyst activation

In a reactor, 0.133 g of palladium bromide, 0.155 g of cobalt(II) acetylacetonate and 3.2 g of tetrabutylammonium bromide were dissolved at 55° C. in 100 g of phenol containing 750 ppm of $H_2O$ (≙ 4 mmol of $H_2O$/100 g). Carbon monoxide (3 l/h) was passed in for one hour by means of a gassing stirrer.

Reaction procedure

To the solution of the activated catalyst were added 4 g of zeolite A (Baylith L 133 from Bayer AG) and 0.4 ml of 25% strength aqueous sodium hydroxide solution. A gas mixture (12 l/h) comprising carbon monoxide and air (1:1) was then passed in for 6 hours and the reaction mixture was subsequently analysed by gas chromatography. The analysis indicated that 0.8% of diphenyl carbonate was present in the reaction mixture.

This experiment was, as described, repeated. The analysis indicated that 0.8% of diphenyl carbonate was present in the reaction mixture.

Example 7

In a reactor, 0.133 g of palladium bromide and 3.2 g of tetrabutylammonium bromide were dissolved at 55° C. in 100 g of phenol. Carbon monoxide (3 l/h) was passed in for one hour by means of a gassing stirrer. To this solution were added 4 g of zeolite A (Baylith L 133 from Bayer AG), 0.153 g of manganese(II) acetylacetonate and 0.302 g of sodium phenoxide as solid. A gas mixture (12 l/h) comprising carbon monoxide and air (1:1) was then passed in for 6 hours and the reaction mixture was subsequently analysed by gas chromatography. The analysis indicated that 2.5% of diphenyl carbonate was present in the reaction mixture.

Example 7a

The experiment was, as described in Example 7, repeated, but with the addition of 0.104 mg (2.6 mmol) of sodium hydroxide in place of the sodium phenoxide. The analysis indicated that 0.8% of diphenyl carbonate was present in the reaction mixture.

Example 7b

The experiment was, as described in Example 7, repeated, but with the addition of 0.4 ml (2.6 mmol) of a 50% strength sodium hydroxide solution in place of the sodium phenoxide. The analysis indicated that 1.4% of diphenyl carbonate was present in the reaction mixture.

Example 8

The experiment was, as described in Example 7, repeated, but with the addition of the sodium phenoxide not as solid but as 15% strength by weight solution in phenol. The analysis indicated that 2.4% of diphenyl carbonate was present in the reaction mixture.

Example 9

The experiment was, as described in Example 7, repeated, but with the addition of potassium phenoxide as solid in place of the sodium phenoxide. The analysis indicated that 2.5% of diphenyl carbonate was present in the reaction mixture.

Example 10

The experiment was, as described in Example 7, repeated, but with the addition of sodium phenoxide trihydrate as solid in place of the sodium phenoxide. The analysis indicated that 2.4% of diphenyl carbonate was present in the reaction mixture.

Example 11

The experiment was, as described in Example 3, repeated, but with the addition of sodium phenoxide as solid in place of 25% strength by weight of aqueous sodium hydroxide solution. The analysis indicated that after 6 hours 2.5% of diphenyl carbonate was present in the reaction mixture.

What is claimed is:

1. A process for preparing an organic carbonate of the formula (I)

$$R\text{—}O\text{—}CO\text{—}O\text{—}R \qquad (I),$$

in which

R is a substituted or not substituted $C_6$–$C_{12}$-aryl, by reaction of an aromatic hydroxy compound of the formula (II), $$R\text{—}O\text{—}H \qquad (II),$$

where

R is as defined above, with carbon monoxide and oxygen at 30°–200° C. and at a pressure of 1–80 bar in the presence of a base, a quaternary salt, a desiccant, a compound of a noble metal of the group VIIIB as catalyst and a cocatalyst selected from the group consisting of the metal compounds of the groups IIIA, IVA, VA, IB, IIB, VIB and VIIB of the Periodic Table of the Elements, wherein the noble metal catalyst is, prior to the reaction, activated by treatment with carbon monoxide in a liquid phase at a temperature of 15°–200° C. and a pressure of 1–300 bar in the presence of the quaternary salt and in the presence or in the absence of the cocatalyst, with the noble metal catalyst being present in the activation mixture in an amount of 0.0001–30% by weight, based on the total reaction mixture.

2. The process of claim 1, wherein the noble metal is palladium.

3. The process of claim 1, wherein the cocatalyst is present in the activation mixture in an amount of 0–40% by weight, based on the total activation mixture.

4. The process of claim 1, wherein the base used is a preformed phenoxide or a solution of a preformed phenoxide.

5. The process of claim 4, wherein the phenoxide contains a maximum of 5 mol of water per mole of phenoxide.

6. The process of claim 5, wherein the phenoxide contains a maximum of 2 mol of water per mol of phenoxide.

7. The process of claim 6, wherein the phenoxide contains a maximum of 1 mol of water per mol of phenoxide.

8. The process of claim 7, wherein the phenoxide is essentially anhydrous.

9. The process of claim 4, wherein from 0.1 to 5 mol of phenoxide is used per mole of noble metal.

10. The process of claim 9, wherein from 0.5 to 2 mol of phenoxide is used per mol of noble metal.

11. The process of claim 10, wherein from 0.9 to 1.3 mol of phenoxide is used per mol of noble metal.

12. The process of claim 1, wherein the quaternary salt used is a tetraalkylammonium or tetraalkylphosphonium salt in an amount of from 0.01 to 50% by weight based on the weight of the reaction mixture.

13. The process of claim 12, wherein the quaternary salt is used in an amount of from 0.5 to 15% by weight, based on the weight of the reaction mixture.

14. The process of claim 1, which is carried out without addition of solvents.

15. The process of claim 1, wherein the dessicant used is a zeolite.

16. The process of claim 1, wherein diphenyl carbonate is prepared from phenol, $O_2$ and CO in the presence of tetrabutylammonium bromide, a cocatalyst, a dessicant and a palladium catalyst activated with carbon monoxide in the presence of a quaternary salt, and also an alkali metal phenoxide.

17. The process of claim 1, wherein the noble metal catalyst is activated at 20°–150° C.

18. The process of claim 17, wherein the noble metal catalyst is activated at 40°–100° C.

19. The process of claim 1, wherein the noble metal catalyst is activated at 1–200 bar.

20. The process of claim 19, wherein the noble metal catalyst is activated at 1–150 bar.

* * * * *